United States Patent [19]
Mucci et al.

[11] Patent Number: 5,154,960
[45] Date of Patent: Oct. 13, 1992

[54] DRAPEABLE SOFT ODOR ABSORBING SHEET MATERIAL

[75] Inventors: Eileen Mucci, 335 Old Orchard Grove, Toronto, Ontario, Canada, M5M 2E7; Ramesh K. Gupta, Oakville; Jacob Leidner, North York, both of Canada

[73] Assignee: Eileen Mucci, Toronto, Canada

[21] Appl. No.: 541,805

[22] Filed: Jun. 21, 1990

[51] Int. Cl.$^5$ .............................................. B32B 1/04
[52] U.S. Cl. ........................................ 428/68; 36/44; 428/198; 428/206; 428/208; 428/244; 428/283; 428/284; 428/323; 428/331; 428/137; 428/138; 428/913
[58] Field of Search ............ 428/68, 74, 198, 206, 428/208, 244, 283, 323, 325, 327, 331, 137, 138, 150, 913; 36/44

[56] References Cited

U.S. PATENT DOCUMENTS

| | | | |
|---|---|---|---|
| Re. 29,501 | 12/1977 | Lapidus | 36/44 |
| 3,842,519 | 10/1974 | Lapidus | 36/44 |
| 4,045,609 | 8/1977 | Hart | 428/253 |
| 4,235,027 | 11/1980 | Singh | 36/44 |
| 4,250,172 | 2/1981 | Mutzenberg et al. | 428/234 |
| 4,411,948 | 10/1983 | Ogino et al. | 428/283 |
| 4,433,024 | 2/1984 | Eian | 428/198 |
| 4,461,099 | 7/1984 | Bailly | 36/44 |
| 4,517,308 | 5/1985 | Ehlenz et al. | 502/401 |
| 4,539,982 | 9/1985 | Bailly | 128/156 |
| 4,815,963 | 3/1989 | Berkhout | 428/325 |

Primary Examiner—James J. Bell
Attorney, Agent, or Firm—Ridout & Maybee

[57] ABSTRACT

Odor absorbing sheet material is formed from a thin flexible substrate sheet on which discrete spaced areas, for example dots, of bonding agent such as latex adhesive are applied. Odor absorbing granules are bonded to the surface of each adhesive area. Since only small portions of the surfaces of the granules adhere to the adhesive, the odor absorbing capacity of the granules is not impaired. A thin flexible permeable cover sheet is applied on the or each granule coated side of the substrate sheet and is attached in a manner which maintains permeability of the assembly so that access of air to the granules is preserved and which does not substantially affect the flexibility of the assembly so that a sheet product with a soft flexibility and drapeable hand is obtained. Preferably, the outer cover sheet of the assembly is an anti-friction porous polymer web such as for example the webs used as facing layers on non-stick or non-adherent wound dressings and bandages.

16 Claims, 2 Drawing Sheets

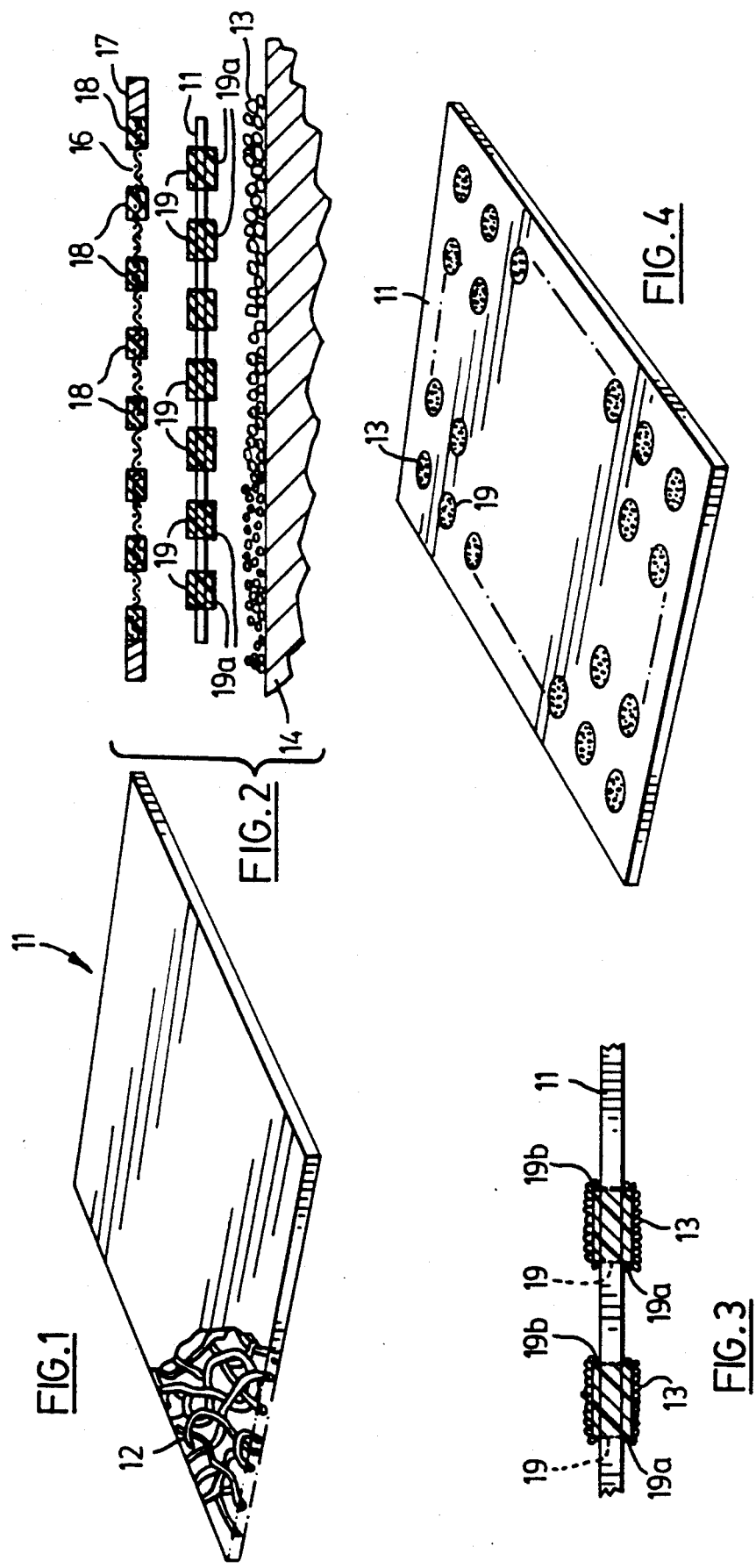

DRAPEABLE SOFT ODOR ABSORBING SHEET MATERIAL

The present invention relates to an odor absorbing sheet material which is readily flexible and has a pliable, drapeable hand. Further, the invention relates to such sheet material which may be provided with a cleanlooking and aesthetically attractive appearance.

The sheet material of the invention is intended for use on an odor-absorbing item in, for example, rooms, empty food storage containers, in association with bedding, storage of clean or soiled laundry, garments or footwear, or in association with the storage of fabric items such as tents, sleeping bags and the like. The material may be used as a hanging or may be draped over furniture in for example, cottages where odors may arise from lack of circulation of air, in between periods of occupation, or in basement rooms to absorb and eliminate musty odors. Pieces may be used within empty coolers, vacuum bottles, picnic baskets, lunch boxes and the like to remove persisting food odors. The material may be applied in the bottom and on the inner sides of laundry hampers or the like, between mattresses and box springs or as a liner or hanging in closets, drawers and the like wherein odors may arise from the storage of clothing items, linens, bedding, or footwear. When used as a hanging, pieces of the sheet material may be hung within closets or the like, for example by being draped over clothes hangers. In addition to being used as a hanging or closet or drawer liner, the sheet material may be placed in pockets provided within hanging garment bags, zippered clothes or footwear storage containers, or single sheets of the sheet material may be placed between layers of clothing disposed in drawers, closets, bags or containers.

Known odor absorbing sheet materials are typically intended for use as odor absorbing insoles for footwear and are formed as self-supporting sheets which are molded or cast from a mixture of odor absorbing granules and a binder. Typically, these sheets have an unattractive grey color as a result of the loading of the odor absorbing material (usually activated carbon), and therefore are not materials of a character or quality such that the consumer would want to place them in close contact with clothing, linens and the like. Further, air filter materials and toxic gas or vapor absorbing sheet materials are known comprising continuous layers or matrices of binding agents retaining absorptive particles such as activated carbon. In some cases, quite complex manufacturing procedures are required for forming these products. Further, the continuous layers or matrices of binding agent tend to impart stiffness to the product which is therefore not of a drapeable flexibility such as the materials of the present invention which are desired to conform to or follow the contours of items such as clothing, hangers, furniture, interior surfaces of containers, hampers etc. to which the sheet materials are desired to be applied. Moreover, with the relatively stiff known absorptive materials there is the risk that if they are bent to a small radius of curvature the stiff layer or matrix of binder or binding agent may break or rupture, resulting in release of the carbon or other absorptive granules with the result that clothing or other items become dirtied and discolored.

The odor absorbing sheet materials of the invention comprise an assembly of a thin flexible substrate sheet on which discrete spaced areas, such as dots, of adhesive are applied on either side of the sheet. The odor absorbing granules are bonded on the surface of these areas. Over the substrate, there extends a thin air permeable cover sheet, which conceals the granules, protects articles to which the sheet material is applied from contact with the granules and provides the sheet material with an aesthetically attractive appearance and pleasant feel. The cover sheet is connected to the substrate with connecting means which allow access of air from the exterior of the cover sheet to the granules. Since the adhesive is not applied continuously over the substrate, this retains essentially its original flexibility and thus the assembly as a whole can have a soft flexibility and a drapeable hand. Further, the sheet material of the invention can be manufactured with relatively simple manufacturing processes and apparatus.

A method of manufacturing one form of sheet material in accordance with the invention will now be described, by way of example only, with reference to the accompanying drawings in which:

FIG. 1 shows partially schematically a nonwoven substrate sheet;

FIG. 2 shows a side view, partially in section and partially schematically, illustrating the operation of screen printing of adhesive dots on the sheet of FIG. 1;

FIG. 3 is a partial side view, partially in section through the imprinted sheet of FIG. 2 and to which granules have been applied;

FIG. 4 is a partially schematic perspective view of the sheet of FIG. 3;

Figure 6:
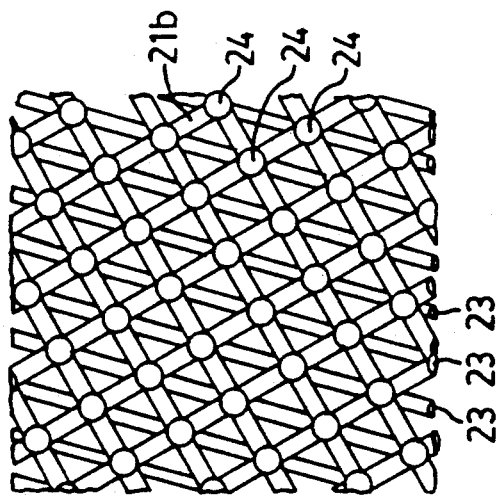
FIGS. 5 and 6 show partially perspective and plan views, respectively, of two different kinds of antifriction cover sheet.

With reference to the drawings, which illustrate successive stages in the manufacture of an example of the sheet material of the invention, FIG. 1 shows one form of thin, flexible substrate sheet 11 which may be used. In this case, the sheet 11 is a porous nonwoven formed of a mat of randomly arranged continuous fibers or staple fibers 12 held together by interconnection at their points of contact through the use of adhesives, solvents, by partial melting of the filaments or fibers by application of heat and pressure, or by needling.

In FIG. 2, the sheet 11 is laid on a layer or bed of odor-absorbing granules 13 disposed on a supporting work surface 14. Over the sheet 11 is laid a silk screen 16 carried in a frame 17. The silk screen is stopped out with a resist medium 18 defining spaced open areas, for example small circular openings. A flowable bonding agent, for example liquid adhesive, is applied to the upper side of the screen 16 while the latter is pressed down on the sheet 11 which in turn is pressed down on the granules 13. The adhesive 19 is thereby deposited on the top and bottom sides and in the interstices of the sheet 11, since it is porous, in the form of spaced areas for example circular dots which preferably are of uniform size and are regularly spaced. The granules 13 adjacent the dots 19a on the lower surface of the sheet adhere to the adhesive. The silk screen 16 is then removed and granules 13 are sprinkled over the top side of the sheet 11 to adhere to the adhesive 19b. The sheet 11 is then shaken to remove excess granules 13.

The resulting sheet material having granules 13 adhering to dots of adhesive 19 on each face of the sheet 11 is shown in FIG. 4 and in cross-section in FIG. 3, wherein the thickness of the adhesive deposit 19 is shown somewhat exaggeratedly. In prior methods of which the applicant is aware for forming odor absorbing sheets, it has been necessary to carefully select the nature of the binder used for binding the odor absorbing granules to avoid deactivation of the granules. However, with applicant's method, the granules adhere on an outer side of the adhesive and are not enveloped or enrobed with the adhesive and therefore the nature of the adhesive is not critical, so that a much wider choice of adhesive materials may be employed.

Each side of the granule coated sheet of FIG. 4 is then covered with an air permeable cover sheet to conceal the granules 13, provide the product with an attractive look and a pleasant feel, and to avoid contact between the granules 13 and articles such as clothing articles to which the odor absorbing sheets are to be applied.

Figure 5:
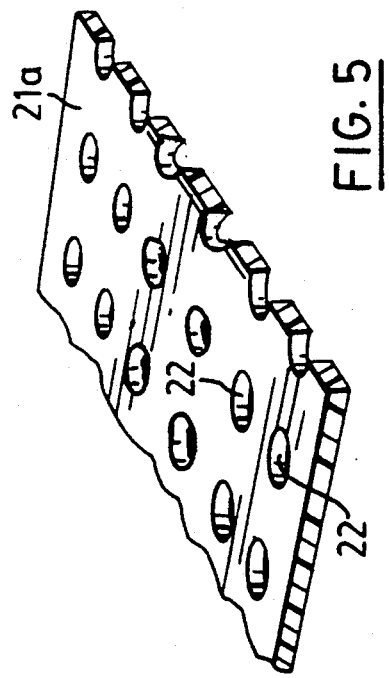

FIGS. 5 and 6 show on a greatly enlarged scale two examples of preferred forms of flexible porous cover sheet. In FIG. 5 the cover sheet is in the form of a thin plastic film 21a provided with regularly spaced and uniform minute perforations 22. FIG. 6 shows a sheet 21b in the form of a lattice of intersecting plastic monofilaments 23 fused together at their points of intersection 24. The lattice 21b is formed from three sets of parallel filaments arranged so that the interstices are minute regular triangles.

Figure 7:
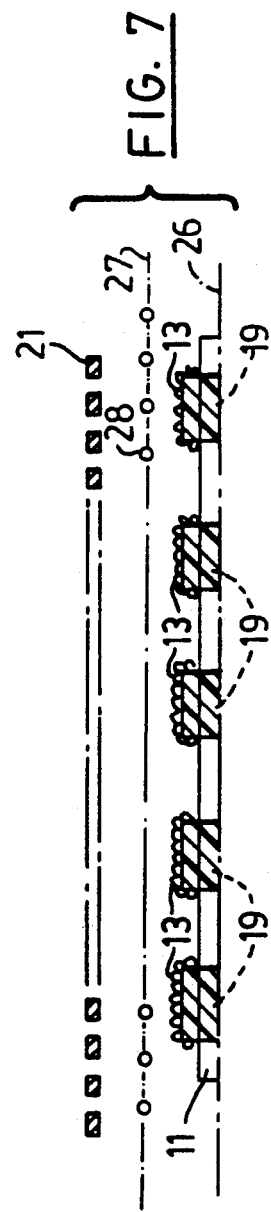
FIG. 7 is a view of the upper half of an assembly of a substrate sheet, connecting sheet and cover sheet, in the course of hot lamination.

FIG. 7 shows an assembly of an air permeable cover sheet together with a granule coated sheet 11 as shown in FIGS. 3 and 4, prior to the assembly being united together by hot lamination. As will be appreciated, for ease of depiction in FIG. 7 only the upper half of the assembly is shown, the lower half being similar and the assembly being symmetrical about the median plane 26. Accordingly, the sheet 11 has the granules 23 on each side and there is a similar cover sheet 21 over the lower side.

In the example shown, the cover sheets 21 are to be united to the granule-coated sheet 11 by hot laminating them together with a porous web 27 of interconnected thermoplastic adhesive filaments 28 seen in cross-section in FIG. 7. The web 27 is of similar structure to the sheet 11 of FIG. 2 but is of a more diffuse open texture and may be the form of web usually referred to as a nonwoven veil of hot melt adhesive.

The laminated product has the cover sheets 21 bonded to the substrate sheet 11 at points at which the filaments 28 melt and bond to the sheets 11 and 21. In the resulting laminated product, the substrate sheet is free to flex in the areas between the adhesive dots 19 and can be bent into a tight radius of curvature without stressing the adhesive 19 and causing rupture of the adhesive or liberation and dispersal of the bound granules 13. Since the thin flexible cover sheet 21 is bonded to the sheet 11 at spaced points, the union of the sheets does not rigidify the assembly which retains essentially the same drapeable hand and soft flexibility as the starting material sheet 11.

Instead of using a porous substrate sheet 11, the sheet 11 may be impermeable, and the dots of adhesive 19 may be applied on one or both sides of the sheet. Preferably, however the sheet 11 is air permeable to encourage circulation of air through the sheet and to improve the odor-absorbing properties of the sheet and preferably the dots of adhesive 19 are applied in such manner that granules can be bonded on both sides of the sheet, in order to increase the loading of absorbent granules per unit area of the sheet 11.

In the event that adhesive 19 and granules 13 are applied on only one side of the sheet 11, only that side of the sheet need have a cover sheet 21 connected to it.

Preferably, the total area occupied by the spaced areas of bonding agent 19, on the or each side of the sheet 11 is about 2 to about 40% of the area of the sheet 11. If the area is much less than 2%, depending on the nature of the granules 13, the sheet 11 may tend to retain insufficient of the granules 13 to provide a satisfactory odor-absorbing capacity. If the area occupied by the adhesive is significantly greater than about 40% of the area of the sheet, depending on the nature of the sheet, the product may tend to be too stiff and will not have the soft flexibility and drapeable hand required for the product. More preferably, the area occupied by the bonding agent 19 on the or each side of the sheet 11 is about 4 to about 25% the area of the sheet 11.

Various procedures may be used for printing adhesive 19, while in a flowable condition, on the sheet 11. In addition to silk screening as described above, gravure printing methods or application of the adhesive through a template may be used, for example.

The adhesive may be a liquid, for example a latex adhesive, which is tacky when in a wet, flowable condition but which after drying forms a non-tacky film. Alternatively, the adhesive may be a hot melt or other thermoplastic adhesive which is a solid at normal room temperatures. In such case, the adhesive in a hot tacky condition may be applied using, for example, the procedure described above with reference to FIGS. 2 to 4, the sheet 11 and the adhesive being maintained hot while the granules 13 are applied to the upper side of the printed sheet. Alternatively, the sheet 11 having dots of hot melt adhesive 19 printed on it in the absence of granules 13 may be heated and passed through a bed of granules 13 in order to allow the granules to bond to the heated adhesive, or a printed sheet 11 carrying the solidified hot melt adhesive may be passed through a bed of heated granules 13, so that the hot granules locally melt the adhesive, render it tacky and thus bond to the tackified adhesive.

In cases where the cover sheet 21 is too transparent and complete concealment of the granules 13 is desired, or where the sheet 21 is too flimsy and weak and there is, for example, a risk that frictional contact with the granules 13 will tear the cover sheet 21, an intermediate flexible porous cover sheet (not shown in the drawings) may be interposed between the or each granule coated side of the sheet 11 and the adjacent outer cover sheet 21. The intermediate cover sheet may be of material similar to or dissimilar from the outer cover sheet 21. The intermediate sheet may likewise be connected to the sheet 11 and the outer sheet 21 using a means of connection which preserves the desired soft flexibility and drapeable hand of the assembled product and allow access of air from the outer side of the outer cover sheet 21 to the granules 13. For example, hot lamination together with an interposed veil of hot melt adhesive filaments may be employed as described above with reference to FIG. 7. If the intermediate cover sheet is very thin and porous, an adequately integral structure can be obtained by hot lamination of the substrate sheet 11, intermediate cover sheet and outer cover sheet 21 with only a single veil of hot melt adhesive between the outer and intermediate cover sheets or between the intermediate sheet and the sheet 11, since the hot melt adhesive penetrates the intermediate sheet.

Other methods which can be used to connect an outer cover sheet 21, with or without an intermediate cover sheet, to the or each granule coated side of the sheet 11 include application of discrete spaced particles or droplets of adhesive to one or both surfaces to be joined and laminating the assembled sheets together. As before, the adhesive may be a liquid tacky adhesive so that the lamination can be conducted in the cold, or may be particles of solid hot melt adhesive so that heat is required to effect the lamination.

The sheet material products obtained as described above may be used for odor absorbing purposes and specific instances of applications of the odor absorbing sheet material have been listed earlier in this specification. Since only a point or small area on the surface of each granule adheres the adhesive 19, the odor absorbing capacity of the granules remains largely unimpaired by contact with the adhesive. Since the cover sheets 21, and any intermediate sheets, are porous, as is the means used for connection of the cover sheets and any intermediate sheets to the substrate sheet 11, and as is preferably also the substrate sheet 11 itself, the product is capable of providing excellent exposure of the odor absorbing granules to the ambient air so that the granules efficiently and effectively absorb odor causing substances.

The substrate sheet 11 may be a fibrous sheet and may be for example a knitted, woven or nonwoven sheet. Preferably it is a nonwoven fabric of the kind illustrated in FIG. 1, by reason of the outstanding thinness, flexibility, permeability and strength of such sheets. Desirably, the sheet 11 has sufficient strength that it will readily withstand handling without tearing,. However, it will be appreciated that if other components of the laminated sheet product confer adequate tear strength, the substrate sheet 11 itself need not have great strength. Examples of suitable materials for the substrate sheet 11 include nonwoven polyester fabrics such as REEMAY 2250 or REEMAY 2200 available from Reemay Inc.

Examples of suitable odor absorbing granules include active clay, alumina, silica gel, odor absorbing polymer particles and carbonaceous particles such as activated carbon granules as available, for example from Cameron Carbon Inc., Baltimore Md., under the identification SG6.

Examples of suitable adhesives include liquid latex adhesives, for example EVA (ethylene-vinyl acetate) latex adhesives as available under the trademarks AIRFLEX 400s and AIRFLEX 400H from St. Lawrence Chemical Inc., Toronto, Canada, and PVA (polyvinyl acetate) latex adhesives, such as that available under the trademark FLEXBOND 149, also from St. Lawrence Chemical Inc.

Further examples include hot melt adhesive materials such as EVA-based formulations, blended for example with waxes and tackifying resins to make the formulations fast-setting. Examples of such materials include the material available under the trademark PE/EVA 232 from Hysol Canada Inc., Scarborough, Ontario, Canada.

The cover sheet 21 and any intermediate cover sheet may be of any of the materials listed above for use as the substrate sheet or may be for example of paper tissue. Preferably, the outer cover sheet 21 is of a smooth, shiny, antifriction, permeable sheet material which provides an aesthetically attractive appearance and will tend to avoid any risk of attachment of the sheet material to items which it contacts in use. Particularly, this will tend to avoid risk of contact with the sheet material tending to damage fine or delicate fabrics or items of apparel. In the preferred form the antifriction outer sheet comprises a non-stick film as used as a facing film for non-stick or non-adherent wound dressings or bandages. One example of such a material is highly perforated polyethylene film e.g. DELNET from Advanced Extrusion Technologies, Middletown, Delaware. Such antifriction materials may have the finely foraminous structure or the fine lattice structure shown in FIGS. 5 and 6 of the accompanying drawings. Examples of such materials include the plastic films used in the non-stick facing layers of MELOLITE dressings available from Smith & Nephew Inc. of Lachine, Quebec, Canada and of TELFA dressings available from Kendall Canada division of CKR Inc., Toronto, Canada. Typically, the openings in such films are about 0.5 mm across.

Examples of liquid or solid adhesives that may be employed in laminating the cover and substrate sheets 21 and 11 together include the liquid latex adhesives and hot melt adhesives mentioned above. Examples of hot melt porous webs useful as the web 27 include hot melt nylon webs such as those available under the designation 5220 nylon and 5230 nylon adhesive webs from HTC Textiles, Quebec, Canada.

Although the above description provides ample information to enable one skilled in the art to make sheet materials in accordance with the invention, for the given.

EXAMPLE 1a

Fabrication of qranule coated sheet

Following the procedure described above with reference to FIGS. 2 and 3, a homogeneous layer of activated carbon SG6 (20×50 mesh) was sprinkled approximately 6 mm thick on a flat clean surface. One sheet of REEMAY 2250 nonwoven polyester fabric was placed on the activated carbon layer. A silk screen was placed on the polyester fabric. The silk screen was of mesh size 74 and was stopped out with resist leaving openings about 6 mm diameter spaced at about 1.3 cm centres. AIRFLEX 400H EVA latex glue was squeegeed through the silk screen at a rate of application (wet) of about 1 g per 100 cm$^2$. As a result, the glue penetrated the fabric and granules of the activated carbon adhered in dot-shaped groups on the lower side of the fabric. The silk screen was then removed, more of the same activated carbon granules were sprinkled on the upper side and excess granules were shaken off. This left carbon granules adhered in dotshaped groups to the upper side of the fabric. The product had the appearance shown in FIG. 4. The total loading of carbon granules was about 1.2 g/100 cm$^2$.

EXAMPLE 1b

Fabrication of laminated sheet material

An assembly was made from the following:
Layer 1: Paper tissue approx. 72 g/m$^2$.
Layer 2: Adhesive web 5220 Nylon (HTC Textiles).
Layer 3: Granule-coated product of Example 1a.
Layer 4: Same as Layer 2.
Layer 5: Same as Layer 1.

This 5-layer construction was laminated together in a hot press for 1 min. at about 150° C.

EXAMPLE 2a

Fabrication of granule coated sheet

The procedure of Example 1a was followed except the openings in the silk screen were approximately 5 mm diameter and spaced approximately at 1 cm centres, and the AIRFLEX 400H adhesive was applied at a rate of about 0.8 g (wet) per 100 cm$^2$. The total loading of carbon granules was about 1.0 g per 100 cm$^2$.

EXAMPLE 2b

Fabrication of laminated sheet material

The procedure of Example 1b was followed except layer 3 consisted of the product of Example 2a.

EXAMPLE 3a

Fabrication of granule coated sheet

The procedure of Example 1a was followed except the openings in the silk screen were about 1.6 mm diameter and spaced at approximately 6 mm centres. The rate of application of the AIRFLEX 400H adhesive was about 0.8 g (wet) per 100 cm$^2$ and the total bonding of carbon granules on the product was about 0.8 g per 100 cm$^2$.

EXAMPLE 3b

Fabrication of laminated sheet material

The procedure of Example 1b was followed except layer 3 consisted of the product of Example 3a.

EXAMPLE 4

Fabrication of laminated sheet material

The procedure of Example 1b could be followed except the construction of the laminate is as follows:
Layer 1: DELNET highly perforated polyethylene film from Advanced Extrusion Technologies.
Layer 2: Adhesive web 5220 nylon.
Layer 3: Paper tissue approx. 72 g/m$^2$.
Layer 4: Granule coated product of Example 1a.
Layer 5: Same as layer 3.
Layer 6: Same as layer 2.
Layer 7: Same as layer 1.

The seven layer construction is laminated together in a hot press for 2 mins. at 150° C.

We claim:

1. Odor absorbing sheet material comprising an assembly of a thin flexible substrate sheet having adhering on at least one side discrete spaced areas of a bonding agent, granules having odor absorbing capacity bonding to the surface of each of said discrete areas, a thin flexible air permeable cover sheet covering at least said one side of the substrate sheet, and means connecting said cover sheet to said substrate sheet, said connecting means allowing access of air from the exterior of the cover sheet to the granules, and said assembly being flexible and having a drapeable hand.

2. Sheet material as claimed in claim 1 having said areas of said bonding agent on each side of the substrate sheet, odor absorbing granules bonded on each of said areas in each side of the substrate sheet, and a cover sheet connected by said connecting means on each side of said substrate sheet.

3. Sheet material as claimed in claim 1 wherein said substrate sheet is a fibrous sheet.

4. Sheet material as claimed in claim 3 wherein said fibrous sheet is nonwoven.

5. Sheet material as claimed in claim 1 wherein said areas of bonding agent total about 2 to about 40% of the area of the substrate sheet.

6. Sheet material as claimed in claim 1 wherein said areas of bonding agent total about 4 to about 25% of the area of the substrate sheet.

7. Sheet material as claimed in claim 1 wherein said bonding agent is a latex adhesive or a hot melt adhesive.

8. Sheet material as claimed in claim 1 wherein areas are printed in a regular pattern on said substrate sheet.

9. Sheet material as claimed in claim 1 wherein the odor absorbing granules are activated clay, alumina, silica gel, odor absorbing polymer particles, or carbonaceous particles.

10. Sheet material as claimed in claim 9 wherein the granules are activated carbon granules.

11. Sheet material as claimed in claim 10 wherein the cover sheet comprising an air permeable anti-friction polymer web.

12. Sheet material as claimed in claim 11 wherein said web comprises a lattice of polymer filaments interconnected at their points of intersection.

13. Sheet material as claimed in claim 11 wherein said web comprises a perforated polymer film.

14. Sheet material as claimed in claim 1 wherein said connecting means comprise particles of thermoplastic adhesive dispersed over said assembly and bonding to said substrate sheet and to said cover sheet.

15. Sheet material as claimed in claim 1 wherein said connecting means comprise a porous web of interconnected thermoplastic adhesive filaments coextensive with said assembly and bonding to said substrate sheet and to said cover sheet.

16. Sheet material as claimed in claim 1 comprising an intermediate air permeable cover sheet interposed between the substrate sheet and the first-mentioned cover sheet, and connecting means connecting together said substrate, intermediate cover and first-mentioned cover sheets and allowing access of air from the exterior of the first-mentioned cover sheet to the granules.

* * * * *